(12) United States Patent
Manolidis

(10) Patent No.: US 11,998,467 B2
(45) Date of Patent: Jun. 4, 2024

(54) STENT DELIVERY FOR VASCULAR SURGERY

(71) Applicant: Spiros Manolidis, Southlake, TX (US)

(72) Inventor: Spiros Manolidis, Southlake, TX (US)

(73) Assignee: Tensor Flow Ventures LLC, Dallas, TX (US)

( * ) Notice: Subject to any disclaimer, the term of this patent is extended or adjusted under 35 U.S.C. 154(b) by 1007 days.

(21) Appl. No.: 16/752,343

(22) Filed: Jan. 24, 2020

(65) Prior Publication Data

US 2020/0237540 A1 Jul. 30, 2020

Related U.S. Application Data

(63) Continuation-in-part of application No. 16/752,265, filed on Jan. 24, 2020, and a continuation-in-part of application No. 16/752,315, filed on Jan. 24, 2020.
(Continued)

(51) Int. Cl.
*A61F 2/90* (2013.01)
*A61B 5/00* (2006.01)
(Continued)

(52) U.S. Cl.
CPC ............ *A61F 2/966* (2013.01); *A61B 5/026* (2013.01); *A61B 5/6862* (2013.01); *A61F 2/848* (2013.01);
(Continued)

(58) Field of Classification Search
CPC .... A61F 2/966; A61F 2/88; A61F 2/90; A61F 2002/8483; A61F 2002/8486;
(Continued)

(56) References Cited

U.S. PATENT DOCUMENTS 4,054,128 A 10/1977 Seufert et al.
4,832,055 A 5/1989 Palestrant
(Continued)

FOREIGN PATENT DOCUMENTS

CN 104116484 A1 10/2014
DE 102016007669 A1 12/2017
(Continued)

OTHER PUBLICATIONS

International Preliminary Report on Patentability for International Application No. PCT/US2020/015447 dated Feb. 17, 2021.
(Continued)

*Primary Examiner* — Suzette J Gherbi
(74) *Attorney, Agent, or Firm* — David W. Carstens; J. Andrew Reed; Carstens, Allen & Gourley, LLP

(57) ABSTRACT

A stent delivery apparatus and/or system including a hollow tubular body with a proximal opening at a proximal end of the hollow tubular body and a distal opening at a distal end of the hollow tubular body. The hollow tubular body can define the proximal opening and the distal opening. A support rod can be passed through the proximal opening and/or the distal opening. The support rod may have a tip, and tip can be olive shaped. A stent may be supported by and/or surround the support rod. The tip of the support rod may also engage with the stent during delivery.

31 Claims, 9 Drawing Sheets

Related U.S. Application Data

(60) Provisional application No. 62/797,933, filed on Jan. 28, 2019, provisional application No. 62/797,932, filed on Jan. 28, 2019, provisional application No. 62/797,944, filed on Jan. 28, 2019.

(51) Int. Cl.
| | |
|---|---|
| *A61B 5/026* | (2006.01) |
| *A61F 2/848* | (2013.01) |
| *A61F 2/88* | (2006.01) |
| *A61F 2/95* | (2013.01) |
| *A61F 2/966* | (2013.01) |
| *A61B 17/11* | (2006.01) |

(52) U.S. Cl.
CPC ............... *A61F 2/88* (2013.01); *A61F 2/90* (2013.01); *A61F 2/95* (2013.01); *A61B 2017/1107* (2013.01); *A61B 2017/1132* (2013.01); *A61F 2002/8483* (2013.01); *A61F 2002/8486* (2013.01); *A61F 2210/009* (2013.01); *A61F 2220/0008* (2013.01)

(58) Field of Classification Search
CPC ............. A61F 2002/9665; A61F 2/848; A61B 2017/1107; A61B 2017/1132; A61B 2017/00336; A61B 17/11
See application file for complete search history.

(56) References Cited

U.S. PATENT DOCUMENTS

| | | | |
|---|---|---|---|
| 4,873,965 A | 10/1989 | Danieli | |
| 5,141,516 A | 8/1992 | Detweiler | |
| 5,349,133 A | 9/1994 | Rogers | |
| 5,492,131 A | 2/1996 | Galel | |
| 5,507,725 A | 4/1996 | Savage et al. | |
| 5,536,236 A | 7/1996 | Yab et al. | |
| 5,562,641 A * | 10/1996 | Flomenblit ............... A61F 2/88 |
| | | | 606/198 |
| 5,573,493 A | 11/1996 | Sauer et al. | |
| 5,733,325 A | 3/1998 | Robinson et al. | |
| 5,735,859 A * | 4/1998 | Fischell ................... A61F 2/95 |
| | | | 606/198 |
| 5,746,766 A | 5/1998 | Edoga | |
| 5,851,218 A | 12/1998 | Lev | |
| 5,968,091 A | 10/1999 | Pinchuk et al. | |
| 6,083,257 A | 7/2000 | Taylor et al. | |
| 6,270,524 B1 | 8/2001 | Kim | |
| 6,361,559 B1 | 3/2002 | Houser et al. | |
| 6,485,513 B1 | 11/2002 | Fan | |
| 6,517,574 B1 | 2/2003 | Chuter | |
| 6,565,581 B1 | 5/2003 | Spence et al. | |
| 6,699,263 B2 * | 3/2004 | Cope ................... A61B 17/0401 |
| | | | 606/232 |
| 6,786,919 B1 | 9/2004 | Escano et al. | |
| 6,899,672 B2 | 5/2005 | Chin et al. | |
| 7,090,637 B2 | 8/2006 | Danitz et al. | |
| 7,476,256 B2 | 1/2009 | Meade et al. | |
| 7,678,068 B2 * | 3/2010 | Levine ...................... A61F 2/04 |
| | | | 604/8 |
| 7,766,962 B1 | 8/2010 | Quinn | |
| 8,097,009 B2 | 1/2012 | Wu et al. | |
| 8,211,025 B2 | 7/2012 | Donaldson et al. | |
| 8,298,161 B2 | 10/2012 | Vargas | |
| 8,360,968 B2 | 1/2013 | Hadani | |
| 8,444,549 B2 | 5/2013 | Viola et al. | |
| 8,512,232 B2 | 8/2013 | Rothberg et al. | |
| 8,615,288 B2 | 12/2013 | Govari et al. | |
| 8,920,482 B2 | 12/2014 | McHugo | |
| 9,220,568 B2 | 12/2015 | Bromander et al. | |
| 9,326,870 B2 | 5/2016 | Berglund et al. | |
| 9,757,856 B2 | 9/2017 | Oyola et al. | |
| 9,820,746 B2 | 11/2017 | Imran | |
| 9,949,692 B2 | 4/2018 | Hunter | |
| 10,299,950 B2 | 5/2019 | Campbell et al. | |
| 10,420,661 B2 | 9/2019 | Hodgkinson et al. | |
| 10,542,931 B2 | 1/2020 | Kuraguntla et al. | |
| 11,033,377 B2 | 6/2021 | Houston et al. | |
| 11,039,838 B2 | 6/2021 | Binmoeller et al. | |
| 11,259,945 B2 | 3/2022 | Berra | |
| 11,491,003 B2 * | 11/2022 | Arbefeuille ............... A61F 2/90 |
| 11,596,408 B2 * | 3/2023 | Lukin .................... A61B 17/11 |
| 11,696,843 B2 | 7/2023 | Pung et al. | |
| 11,724,009 B2 | 8/2023 | Paquin et al. | |
| 2001/0004696 A1 | 6/2001 | Roberts et al. | |
| 2002/0029076 A1 * | 3/2002 | Yee ......................... A61F 2/966 |
| | | | 606/108 |
| 2002/0099405 A1 | 7/2002 | Yurek et al. | |
| 2002/0099432 A1 * | 7/2002 | Yee ........................... A61F 2/95 |
| | | | 623/1.11 |
| 2002/0143347 A1 | 10/2002 | Cole et al. | |
| 2002/0151957 A1 | 10/2002 | Kerr | |
| 2003/0135266 A1 * | 7/2003 | Chew ......................... A61F 2/91 |
| | | | 623/1.16 |
| 2003/0216801 A1 | 11/2003 | Tweden et al. | |
| 2003/0225445 A1 | 12/2003 | Derus et al. | |
| 2004/0082945 A1 | 4/2004 | Clague et al. | |
| 2004/0116999 A1 | 6/2004 | Ledergerber | |
| 2004/0167604 A1 | 8/2004 | Stinson | |
| 2005/0049480 A1 | 3/2005 | Gray | |
| 2005/0154444 A1 | 7/2005 | Quadri | |
| 2005/0154448 A1 | 7/2005 | Cully et al. | |
| 2006/0052736 A1 | 3/2006 | Tweden et al. | |
| 2006/0074478 A1 | 4/2006 | Feller | |
| 2006/0149349 A1 | 7/2006 | Garbe | |
| 2006/0211984 A1 | 9/2006 | Blank et al. | |
| 2007/0055339 A1 | 3/2007 | George et al. | |
| 2007/0067014 A1 | 3/2007 | Ke et al. | |
| 2007/0106373 A1 | 5/2007 | Houston et al. | |
| 2007/0142711 A1 | 6/2007 | Bayer et al. | |
| 2007/0179598 A1 | 8/2007 | Duerig | |
| 2008/0132906 A1 * | 6/2008 | Rasmussen ............. A61F 2/966 |
| | | | 606/108 |
| 2008/0255653 A1 | 10/2008 | Schkolnik | |
| 2009/0023998 A1 | 1/2009 | Ratnakar | |
| 2009/0171437 A1 | 7/2009 | Brocker et al. | |
| 2009/0281557 A1 | 11/2009 | Sander et al. | |
| 2009/0287293 A1 | 11/2009 | Mailhot | |
| 2010/0030320 A1 | 2/2010 | Feller | |
| 2010/0168835 A1 | 7/2010 | Dorn | |
| 2010/0217082 A1 | 8/2010 | Ito et al. | |
| 2010/0262171 A1 | 10/2010 | Wu et al. | |
| 2011/0190870 A1 | 8/2011 | Hastings et al. | |
| 2011/0264196 A1 | 10/2011 | Savage et al. | |
| 2012/0071721 A1 | 3/2012 | Remijan et al. | |
| 2012/0123464 A1 | 5/2012 | Rasmussen et al. | |
| 2012/0290072 A1 | 11/2012 | Theobald et al. | |
| 2013/0035751 A1 | 2/2013 | Shalev | |
| 2013/0144380 A1 | 6/2013 | Quadri et al. | |
| 2013/0190741 A1 | 7/2013 | Moll et al. | |
| 2013/0245745 A1 * | 9/2013 | Vong ...................... A61F 2/885 |
| | | | 623/1.22 |
| 2013/0331927 A1 | 12/2013 | Zheng et al. | |
| 2014/0081415 A1 | 3/2014 | Ruberti et al. | |
| 2014/0228936 A1 | 8/2014 | Kassab et al. | |
| 2014/0236064 A1 | 8/2014 | Binmoeller et al. | |
| 2014/0277442 A1 | 9/2014 | Seddon et al. | |
| 2014/0303599 A1 | 10/2014 | Heideman et al. | |
| 2015/0328022 A1 | 11/2015 | Hansen et al. | |
| 2015/0366439 A1 | 12/2015 | Luo et al. | |
| 2016/0120638 A1 | 5/2016 | Michalak | |
| 2016/0242940 A1 | 8/2016 | Krautkremer et al. | |
| 2016/0256610 A1 | 9/2016 | Zhou et al. | |
| 2016/0310077 A1 | 10/2016 | Hunter et al. | |
| 2017/0079785 A1 | 3/2017 | Li | |
| 2017/0086929 A1 | 3/2017 | Moll et al. | |
| 2017/0128072 A1 | 5/2017 | Wang et al. | |
| 2017/0296038 A1 | 10/2017 | Gordon et al. | |
| 2017/0330665 A1 | 11/2017 | Zareei et al. | |
| 2018/0207007 A1 | 7/2018 | Giasolli et al. | |
| 2019/0239879 A1 | 8/2019 | Zilla et al. | |
| 2020/0094398 A1 | 3/2020 | Young | |

(56) References Cited

U.S. PATENT DOCUMENTS

| | | | |
|---|---|---|---|
| 2020/0170776 A1 | 6/2020 | Folan | |
| 2020/0237534 A1* | 7/2020 | Manolidis | A61B 5/026 |
| 2020/0237540 A1 | 7/2020 | Manolidis | |
| 2021/0052403 A1* | 2/2021 | Chu | A61F 2/88 |
| 2021/0077247 A1* | 3/2021 | Shalev | A61F 2/07 |
| 2021/0205007 A1* | 7/2021 | Anderson | A61B 18/1492 |
| 2021/0393424 A1 | 12/2021 | McWeeney et al. | |
| 2022/0273365 A1 | 9/2022 | Rege et al. | |
| 2022/0303150 A1 | 9/2022 | Jensen et al. | |
| 2023/0048537 A1* | 2/2023 | Arbefeuille | A61F 2/89 |
| 2023/0132550 A1* | 5/2023 | Vong | A61F 2/844 623/1.11 |
| 2023/0277294 A1 | 9/2023 | Folan | |
| 2023/0310186 A1 | 10/2023 | Nagano et al. | |
| 2023/0355381 A1 | 11/2023 | Peckels et al. | |

FOREIGN PATENT DOCUMENTS

| | | | |
|---|---|---|---|
| EP | 2063823 A2 | 6/2009 | |
| GB | 2452480 A | 11/2009 | |
| JP | 2012065933 A | 4/2012 | |
| WO | 9415549 A1 | 7/1994 | |
| WO | 9423669 A1 | 10/1994 | |
| WO | 0045737 A1 | 8/2000 | |
| WO | 02056798 A2 | 7/2002 | |
| WO | 2008025855 A2 | 3/2008 | |
| WO | 2008066917 A1 | 6/2008 | |
| WO | 2009091899 A2 | 7/2009 | |
| WO | 2011116913 A1 | 9/2011 | |
| WO | WO2011116913 A1 | 9/2011 | |
| WO | 2016069274 A1 | 5/2016 | |
| WO | 2016134148 A1 | 8/2016 | |
| WO | 2018005861 A1 | 1/2018 | |
| WO | WO18005861 A1 | 1/2018 | |
| WO | 2018068106 A1 | 4/2018 | |

OTHER PUBLICATIONS

International Search Report and Written Opinion issued by ISA/US on Jun. 15, 2020 for International Application No. PCT/US2020/015444.

DE102016007669_google_translation.

CN104116484_google_translation.

International Search Report and Written Opinion issued by ISA/US on Apr. 22, 2020 for International Application No. PCT/US2020/015447.

International Search Report and Written Opinion issued by ISA/US on Apr. 28, 2020 for International Application No. PCT/US2020/015439.

\* cited by examiner

STENT DELIVERY FOR VASCULAR SURGERY

CROSS-REFERENCE TO RELATED APPLICATION

The present disclosure claims priority to and is a non-provisional conversion of U.S. Provisional Patent Application No. 62/797,944, filed Jan. 28, 2019, and is a continuation-in-part of U.S. patent application Ser. No. 16/752,265 filed Jan. 24, 2020, which claims priority from U.S. Provisional Patent Application No. 62/797,932, filed Jan. 28, 2019, and is a continuation-in-part of U.S. patent application Ser. No. 16/752,315 filed Jan. 24, 2020, which claims priority from U.S. Provisional Patent Application No. 62/797,933, filed Jan. 28, 2019, all of which is incorporated herein by reference in its entirety for all purposes.

TECHNICAL FIELD

The present invention relates to a stent and the delivery of said stent. More particularly, and not by way of limitation, the present invention is directed to an apparatus, system, or method for sutureless surgery involving a stent and delivery of said stent.

BACKGROUND

There are many different types of surgeries that can be conducted daily in hospitals across the world. One such surgery is free flap reconstruction. Free flap reconstruction is a well-established method of reconstruction of both soft tissue and bone or composite defects in a wide variety of surgeries. Free flaps are used in order of frequency in: head and neck reconstruction, breast reconstruction, orthopedic surgery and a variety of other specialties. Head and neck surgery in particular is a heavy user of free flap reconstruction. This is due to the complexity of defects in a critical area where restoration of functions such as deglutition, phonation, and mastication is of paramount importance in addition to cosmesis.

Free flap reconstruction involves the transfer of tissue from a distant part of the body to the area that needs to be reconstructed. The principle in operation behind this concept is that tissues in the body are supplied in a segmental function. That is that a segment of skin, subcutaneous, tissue, fascia, muscle, bone or any combination of these can be harvested according to specific location. The transfer of tissue is completed when the free flap vessels (artery and vein) are joined to the donor vessels and then the flap is set into the defect.

Donor vessels, are selected from appropriate vessels to match the diameter of the recipient vessels (free flap vessels). In the neck, these are usually branches of the external carotid artery and one of the many veins in the head and neck or the jugular vein itself. Each of the donor vessels are dissected from surrounding tissue, and their edges prepared for anastomosis. In free flap reconstruction, vessels are raised in situ and the vascular supply is dissected out carefully and a traumatically. The vascular supply is then sectioned, preferably at a length of vessel that is appropriate for an anastomosis without tension. This is not always possible as different free flaps have different lengths of vessels according to where they are harvested. For example, a free rectus vascular pedicle may have a max length of 8 cm, while a radial forearm vascular pedicle may have a max length of 15-20 cm.

Once the vessels are extracted from the appropriate location, the edge preparation begins. The vessel preparation process can take approximately one hour and is performed under optimal conditions with an operating microscope and/or magnifying loops. Considerable skill is required that comes with prolonged surgical training. The anastomoses (joining) themselves are approximately 20 minutes per vessel anastomosis. Venous couplers reduce the amount of time required for venous anastomoses. However, these venous couplers still require suturing for each venous anastomoses, taking considerable time and increasing the time a patient is under anesthesia. There are two general types of anastomoses, an end to end and an end to side. An end-to-end anastomoses is preferred because it is performed rapidly without additional problems and because the vascular dynamics are that of linear flow which gives lesser complication rates. End to end anastomoses account for the majority of vessel joining. However, currently these operations and/or couplings still require significant suturing time, that can lead to other complications.

Thus, it would be advantageous to have an apparatus, system, or method for an improved stent and stent delivery for vascular surgery that overcomes the disadvantages of the prior art. The present disclosure provides such an apparatus, system, or method.

BRIEF SUMMARY

The present disclosure is directed to a stent and delivery of said stent during open surgery. Thus, in one aspect, the present disclosure is directed to a stent that may self-modify, or self-expand during or upon delivery.

In another aspect, the present disclosure is directed to a stent that may be delivered with an outer sheath or protective layer. In yet another aspect, the present disclosure is directed to a stent that may be delivered through a syringe or push release mechanism.

Therefore, in one aspect, the present disclosure is directed to a modified self-expanding stent that may be used to perform anastomoses with novel carriers for the endoluminal application of the stent. The stent may have anchor points or atraumatic points.

Thus, in one aspect, the present disclosure is directed to rapidly performing anastomoses without vessel preparation or suturing. In another aspect, the present disclosure is directed to lengthening the pedicle during grafts and/or distention of the lumen of the vessel during stent operation.

BRIEF DESCRIPTION OF THE DRAWINGS

The novel features believed characteristic of the disclosure are set forth in the appended claims. The disclosure itself, however, as well as a preferred mode of use, further objectives and advantages thereof, will be best understood by reference to the following detailed description of illustrative embodiments when read in conjunction with the accompanying drawings, wherein:

DETAILED DESCRIPTION

An embodiment of the disclosure will now be described. It should be noted that while vascular, and/or microvascular surgeries and/or surgical methods will be described herein, the present disclosure could also be utilized in any number of surgeries, including, but not limited to those for, the head, neck, sinus, nasal, ear, heart, lung, arteries, veins, brain, nerves, organs, vessels, and/or any other human or animal surgery. While the description will be related to operations on human, it would be understood that those in the veterinarian field could also benefit from the present disclosure.

Descriptions herein will be made with respect to a gravitational reference, but such descriptions should not be considered limiting. As it would be understood, unless otherwise noted a reference to a left, or right of an object could be mirrored or flipped, similarly unless otherwise noted a reference to up or down could be mirrored or flipped.

The stents, and/or stent delivery mechanisms disclosed herein can be manufactured, made, and/or formed with any number of materials, including, but not limited to, wood, metal, plastic, synthetics, carbon fibers, or other materials.

Figure 1A:
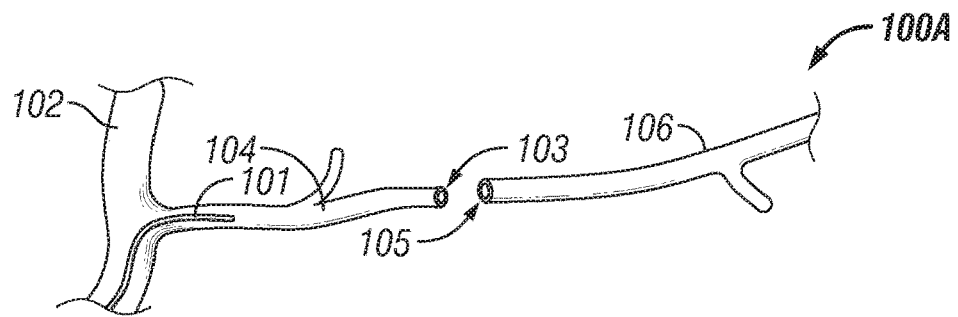
FIG. 1A is an illustration of a proposed anastomosis site.

FIG. 1A is an illustration of a proposed anastomosis site. A vessel system 100A can include an artery 102, a donor vessel 104, and/or a recipient vessel 106. In at least one version, the donor vessel 104 has a vessel anastomosis site 103, and the recipient vessel 106 has a vessel anastomosis site 105 that can be coupled together. The anastomosis site(s) 103/105 can be coupled together with a stent, magnetic stent, and/or expandable stent from unprepared or semi-prepared sites. To allow for a blood flow 101 to be restored to the vessels, arteries, and/or tissue in a decreased amount of time.

Figure 1B:
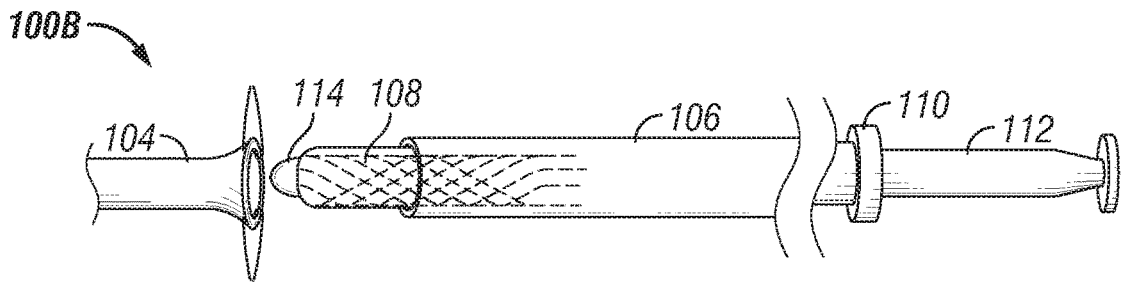
FIG. 1B is an illustration of a stent delivery device and stent.

FIG. 1B is an illustration of a stent delivery device 110 and stent 108. A vessel system 100B can be repaired utilizing a stent 108, and a stent deliver device 110. The stent 108 can include a hollow tubular body or tubular stent body, a first end or proximal end of the hollow tubular body, a second end or distal end of the hollow tubular body, connection node(s), and/or structure member(s). A stent delivery device 110 can include a delivery tip 114, a plunger 112, and/or a connecting shaft or support rod 199. In at least one embodiment, the plunger 112 is a first section of the connecting shaft, and the support rod 199 is the second section of the connecting shaft and is coupled to the first section to create a connecting shaft. In at least one example, the stent 108 is delivered to a vessel 104/106 by the stent delivery device 110. The stent 108 can have a fixed expansion point, or be expandable upon delivery by the stent delivery device 110.

Figure 1C:
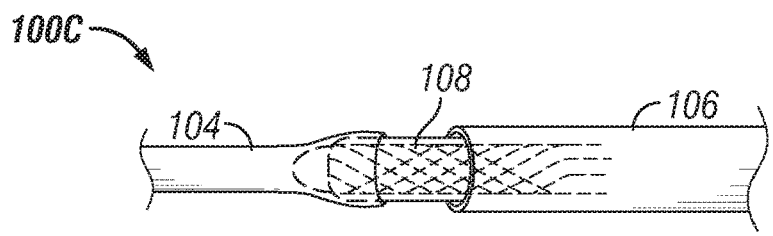
FIG. 1C is an illustration of a stent being placed within both the donor and recipient vessels.

FIG. 1C is an illustration of a stent 108 being placed within both a donor vessel 104 and a recipient vessel 106. A vessel system 100C can be repaired utilizing the stent 108. In at least one version, the stent 108 is expandable, and the expansion occurs when the delivery tip (not illustrated) passes through the stent 108. The expansion can allow anchor(s) (not illustrated) to secure the stent in a specific location within the vessels 104/106.

Figure 1D:
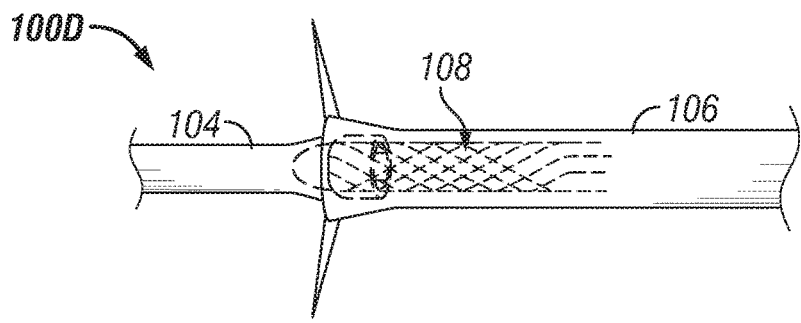
FIG. 1D is an illustration of a stent being secured within the recipient vessel.

FIG. 1D is an illustration of a stent 108 being secured within the recipient vessel 106. A vessel system 100D can be repaired utilizing a stent 108 within the donor vessel 104 and the recipient vessel 106. The stent 108 can be delivered and/or secured within the vessels 104/106 utilizing the stent delivery tool (not illustrated). In at least one version, a tool may be used to provide a mechanism to pull a vessel 104 or 106 over the stent 108.

Figure 1E:
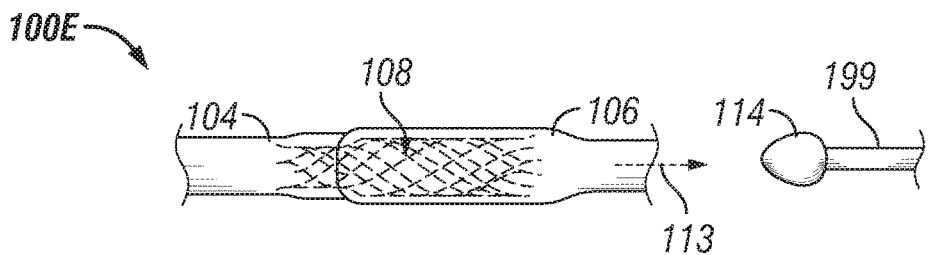
FIG. 1E is an illustration of the stent delivery device removal.

FIG. 1E is an illustration of the stent delivery device removal. A vessel system 100E can be repaired when a stent 108 is secured within, and/or around the vessels and/or tissue. For example, a donor vessel 104 can be secured to a stent 108 through interfacing of the stent with the donor vessel. In at least one version, the stent 108 has anchor(s) (not illustrated) that allow the donor vessel 104 to be secured with the stent 108, and then a recipient vessel 106 can also be secured on the other end of the stent 108 through anchor(s) (not illustrated). The stent delivery device (not illustrated) can then be removed from the vessels 104/106 through a force 113. The force 113 can be created by an action on or to a plunger or another motion that in at least one version retracts the delivery tip 114 through the stent 108. The delivery tip 114 then provides for an expansion force that pushes against the inner surface of the stent 108 causing an expansion of the stent 108 to occur, increasing the interfacing of the stent 108 to the vessels 104/106.

Figure 2A:
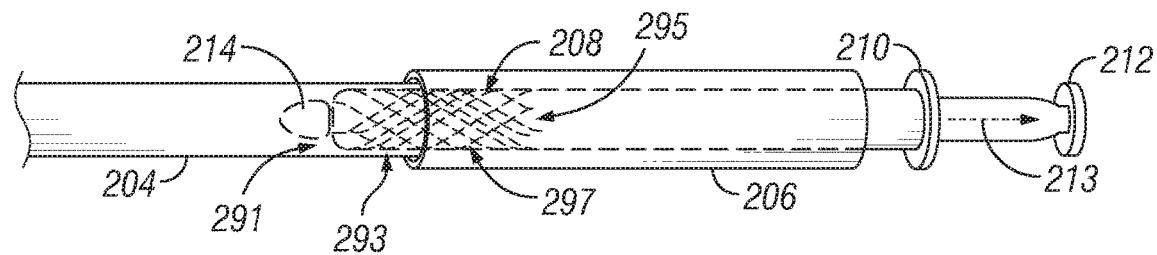
FIG. 2A is an illustration of a stent delivery device and stent.

FIG. 2A is an illustration of a stent delivery device 210 and stent 208. A stent delivery system 200A can include a stent 208 and a stent delivery device 210. The stent deliver device 210 can include a tubular structure or hollow tubular body, a shaft (not illustrated), a plunger 212, and/or a delivery tip 214.

Figure 2B:
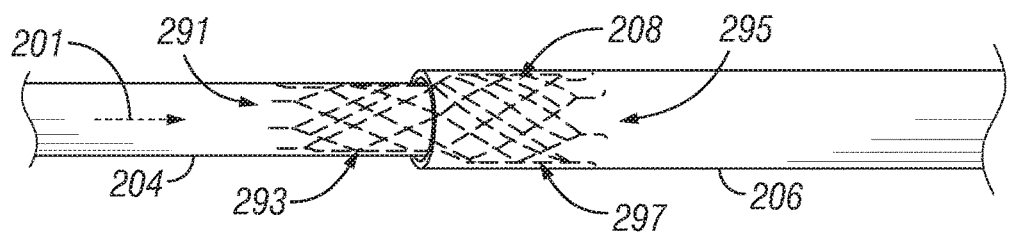
FIG. 2B is an illustration of a stent secured within the vessels.

In at least one version, the stent delivery device 210 can house a stent 208 within a tubular structure with the stent surrounding a shaft (not illustrated) coupled to a plunger 212. When the plunger is depressed, or a delivery force (not illustrated) is applied the stent 208 exits the tubular structure and is delivered to a donor vessel 204 and/or a recipient vessel 206. After delivery, a retraction force 213 can be applied causing the delivery tip 214 to traverse, and/or travel through the cavity and/or hollow tubular structure of the stent 208. In would be understood, that a force applied in a first direction opposite the retraction force 213 may allow for the placement and/or delivery of the stent 208 into a vessel. The travel of the delivery tip 214 through the stent 208 can trigger an expansion of the stent 208. Alternatively, the delivery tip 214 can traverse and/or travel through the stent 208 without triggering and/or initiating an expansion FIG. 2B is an illustration of a stent 208 secured within a donor vessel 204 and a recipient vessel 206. A stent delivery system 200B can provide a stent 208 for the repair and securing of vessels and/or tissue. In at least one version, the stent 208 is placed within two vessels, a donor vessel 204 and a recipient vessel 206 to allow for and/or increase the blood flow 201 between the vessels 204/206. In at least one example, the stent delivery system 200 is utilized in a manner that the stent is delivery against a blood flow 201. Some versions of the stent 208 can also allow for expansion and/or compression from a first state to a second state. The stent 208 can include a hollow tubular body defining a cavity, a first end or proximal end 297 of the hollow tubular body, a second end or distal end 293 of the hollow tubular body, connection node(s), and/or structure member(s). In at least one example, the proximal end 297 of the hollow tubular body defines a proximal opening 295, and the distal end 293 of the hollow tubular body devices a distal opening 291. In at least one example, the stent 208 is manufactured and/or constructed of biodegradable materials to allow for the disintegration of the stent within a few days, weeks, or months after delivery, such as, but not limited to 1 day, 2 days, 3 days, 5 days, 1 week, 1.5 weeks, 2 weeks, 2.5 weeks, 3 weeks, 4 weeks, 1 month, 5 weeks, six weeks, 7 weeks, 8 weeks, 2 months, 9 weeks, 10 weeks, 11 weeks, 12 weeks, 3 months, 4 months, 6 months, 9 months, or 12 months.

Figure 3A:
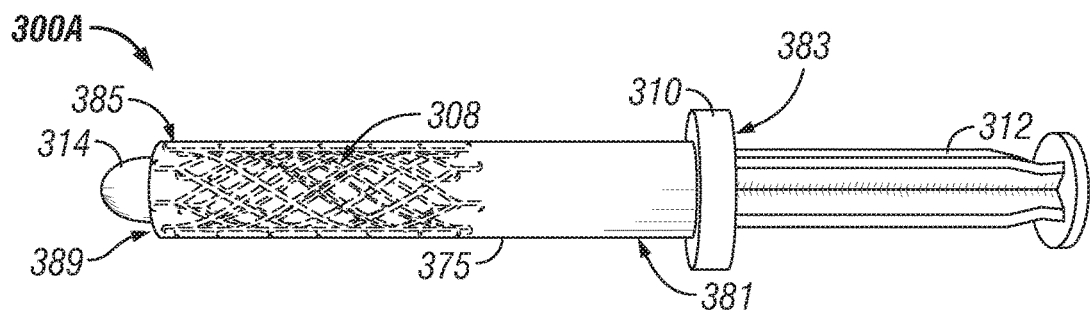
FIG. 3A is an illustration of a stent deliver device.

FIG. 3A is an illustration of a stent deliver system 300A. The stent delivery system 300A can include a stent 308, and/or a stent delivery device 310. The stent delivery device 310 can include a plunger 312, a deliver tip 314, a shaft (not illustrated) coupling the plunger 312 and the delivery tip 314, and a tubular body 375. The tubular body 375 can contain and/or support a stent 308 within or outside the tubular body 375. The stent delivery device 310 can have a first end or proximal end 381 that defines a proximal end opening 383 of the tubular body or hollow tubular body 375. Additionally, the stent delivery device 310 can also have a second end or distal end 385 that defines a distal opening 389.

Figure 3B:
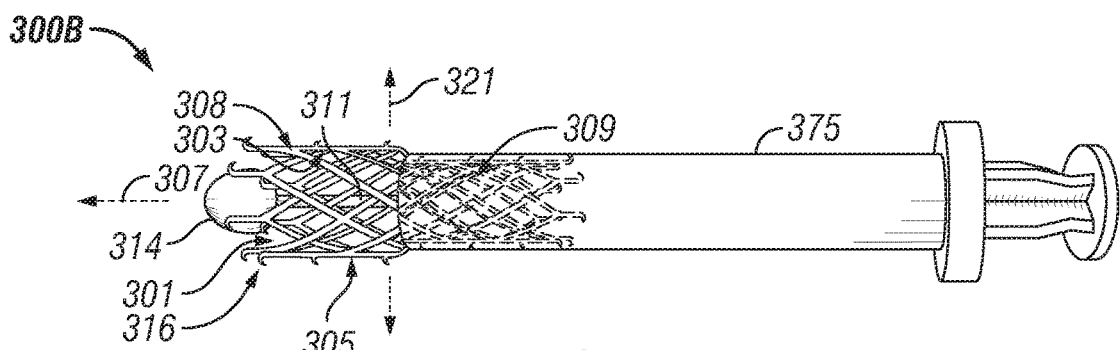
FIG. 3B is an illustration of a stent delivery device with the stent partially delivered.

FIG. 3B is an illustration of a stent delivery system 300B with the stent 308 partially delivered. The stent delivery system 300B provides a delivery mechanism for a stent 308 through the stent delivery device 310. In at least one version, the stent delivery device 310 includes a tubular body 375. The tubular body 375 contains and/or supports the stent 308 during transport, delivery, expansion, and/or compression. A plunger 312 coupled to a shaft 311 and/or the delivery tip 314 can be utilized to move the stent 308 within and/or along the tubular body 375. As the stent 308 is moved a distance 307 out from, or off of the tubular body 375 it may expand 321 and/or compress. The delivery tip 314 can be utilized to increase the expansion 321 upon retraction, and/or traversal through the body of the stent 308. As the stent 308 expands and/or contracts/compresses anchor(s) 316 along the inner surface, outer surface, and/or the ends of the stent 308.

Figure 4A:
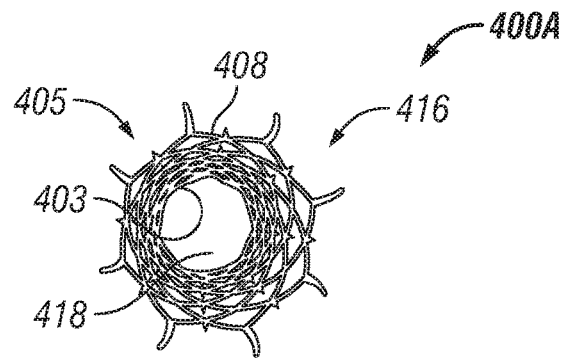
FIG. 4A is an illustration of a coil stent in a longitudinal or end view.

FIG. 4A is an illustration of a stent 408 in a longitudinal or end view. The stent 408 can include a stent body that defines a cavity 418. The cavity 418 can expand, and/or contract based on the state of the stent 408. The inner surface 403 and/or outer surface 405 of the stent 408 can include anchor(s) 416 at a first end 407, a second end 409, and/or along one of the surfaces. In at least one version, the stent 408 is configured to allow for a change of state, for example, an expansion or compression from a first state to a second state.

Figure 4B:
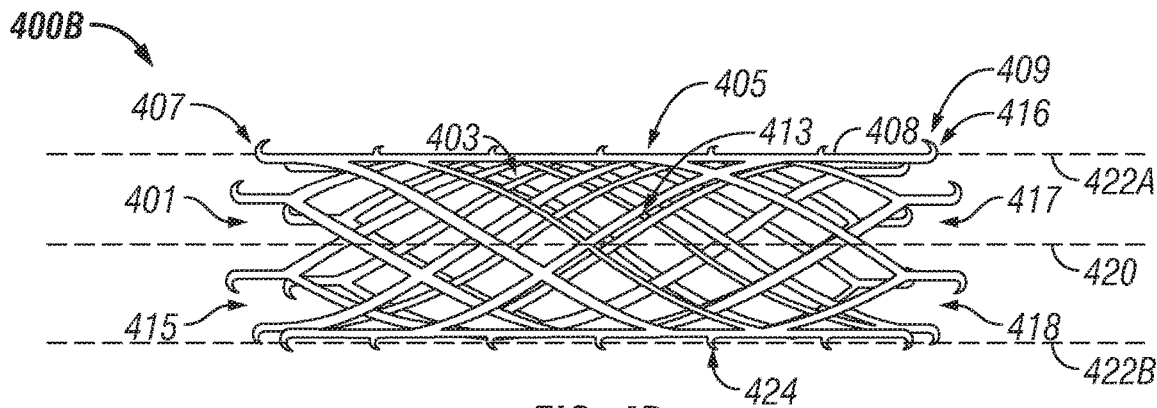
FIG. 4B is an illustration of a coil stent in a side view.

FIG. 4B is an illustration of a stent 408 in a side view. The stent 408 can include a stent body 413 and/or hollow tubular structure 401 define a cavity that traverses the stent 408. The cavity 418 can have a first opening 415 and a second opening 417 at a first or proximal end 407 of the stent 408, or a second or distal end 409 of the stent 408 respectively. The stent 408 can have a first plane 422A parallel with the outer surface 405 of the stent 408, and a second plane 422B parallel with the outer surface of the stent 408. The cavity can also, in at least one example, surround a central plane 420 that is equal distance from the first plane 422A and the second plane 422B. The stent 408 can include end anchor(s) 416 at a first end of the stent 408, and/or a second end of the stent 408, and/or body anchor(s) 424 along the outer surface or inner surface 403 of the stent 408.

Figure 5A:
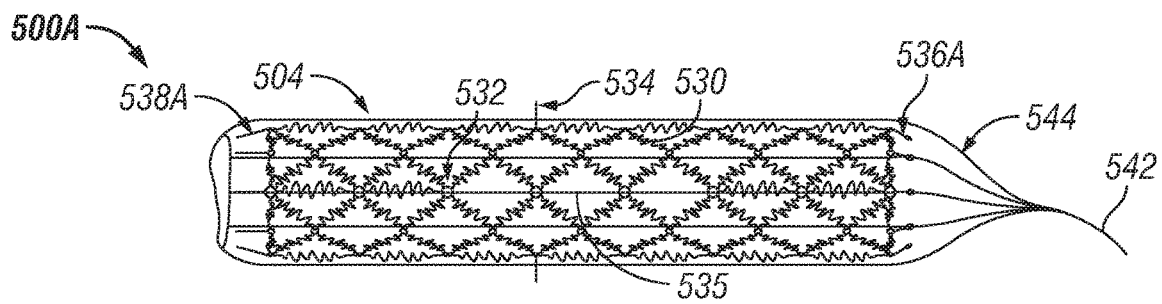
FIG. 5A is an illustration of an expandable stent with sheath.

FIG. 5A is an illustration of a stent delivery system 500A. The stent delivery system 500A can include a stent 508 with sheath, cover, or transport device 540. The stent 508 can include body anchor(s) 534, end anchor(s) 536A, end anchor(s) 538A, structural member(s) 530, and/or connection node(s) 532. In at least one version, the structural member(s) 530 can include expandable member(s) and non-expandable member(s) 535 and the connection node(s) can include magnetic and non-magnetic connection node(s).

The sheath, cover, or transport device 540, can include perforation(s) 544 and/or a needles 542. The perforation(s) 544 can allow the sheath, cover, or transport device 540 to be removed with relative ease because it will separate at the perforation(s) 544 to avoid being caught on anchor(s) 534, 536, 538. In at least one example, the sheath or cover may be used in combination with a transport device creating a barrier between the stent and the transport device.

Figure 5B:
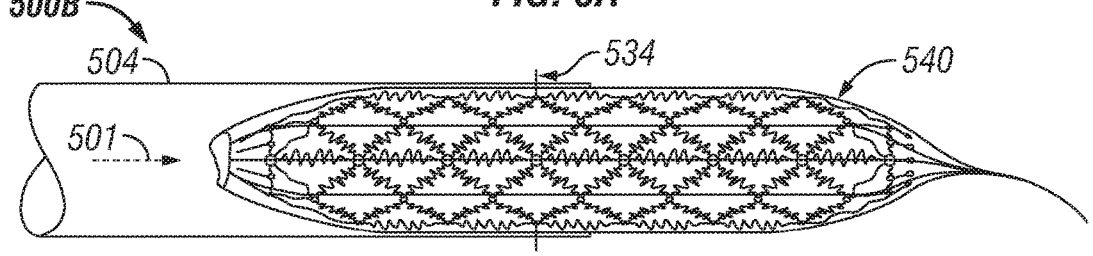
FIG. 5B is an illustration of an expandable stent secured within a donor vessel.

FIG. 5B is an illustration of a stent delivery system 500B. The stent delivery system 500B can include a sheath, cover, or transport device 540, and a stent 508. The stent 508 can include body anchor(s) 534. In at least one example, the donor vessel 504 can be coupled to the stent 508 via the body anchor(s) 534.

Figure 5C:
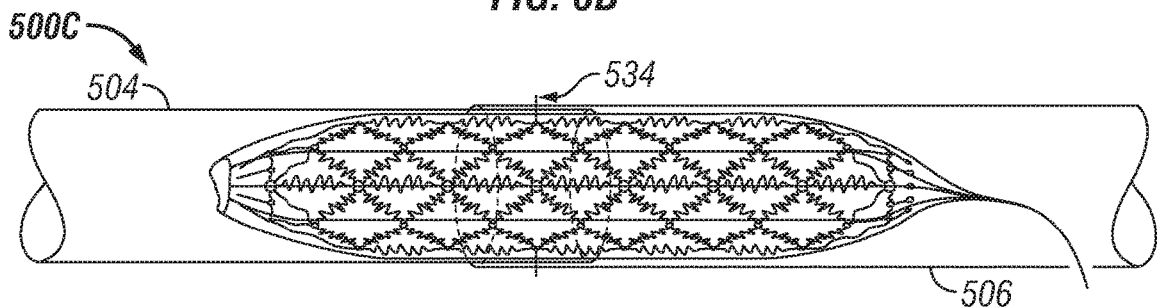
FIG. 5C is an illustration of an expandable stent secured within a donor and recipient vessel.

FIG. 5C is an illustration of a stent delivery system 500C. The stent delivery system 500C can include a sheath, cover, or transport device 540, and a stent 508. The stent 508 can include body anchor(s) 534. In at least one example, the donor vessel 504 can be coupled to the stent 508 via the body anchor(s) 534, along with the recipient vessel 506. In at least one example, the sheath, cover, or transport device 540 can be prepared for removal through an opening in a vessel and/or tissue.

Figure 5D:
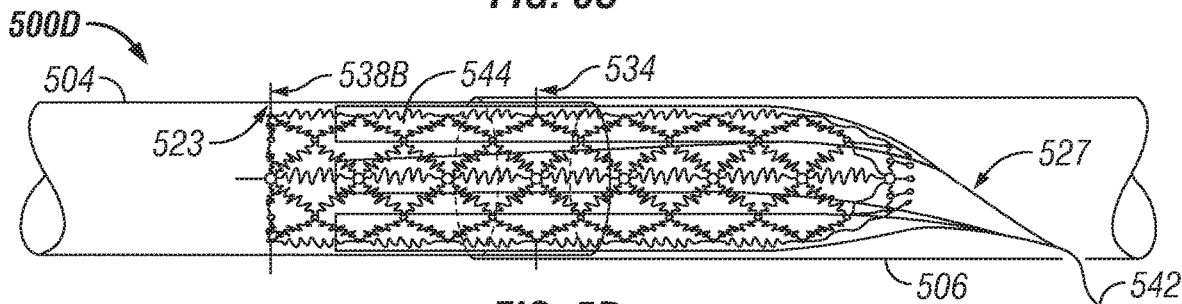
FIG. 5D is an illustration of an expandable stent in a partially expanded state.

FIG. 5D is an illustration of a stent delivery system 500D. The stent delivery system 500D can include a sheath, cover, or transport device 540, and a stent 508. The stent 508 can include body anchor(s) 534, end anchor(s) 536A, and/or end anchor(s) 538B. In at least one example, the donor vessel 504 can be coupled to the stent 508 via the body anchor(s) 534, along with the recipient vessel 506. The end anchor(s) 538B can be expanded and/or transitioned from a first state, to a second state that allows for the end anchor(s) 538B can interface and/or couple 523 with vessels and/or tissue. The expansion and/or transition can result from the removal of the sheath, cover, or transport device 540 from the area of the stent 508 including the end anchor(s) 538B. In at least one version, the sheath, cover, or transport device 540 is removed through an opening 527 in vessels or tissue utilizing a needle 542 coupled to the sheath, cover, or transport device 540. In some versions, the sheath, cover, or transport device 540 can be separated along perforation(s) 544 that allow sheath, cover, or transport device 540 to pass the anchor(s) 534, 536, and/or 538.

Figure 5E:
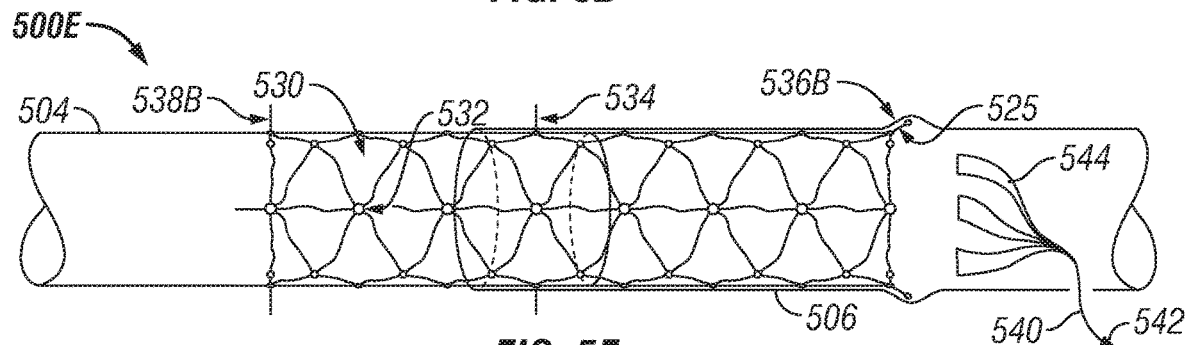
FIG. 5E is an illustration of an expandable stent in a fully expanded state.

FIG. 5E is an illustration of a stent delivery system 500E. The stent delivery system 500E can include a stent 508, and a sheath, cover, or transport device 540. The stent 508 can include structural member(s) 530, connection node(s) 532, end anchor(s) 536B, body anchor(s) 534, and/or end anchor(s) 538B. The end anchor(s) 536B/538B can be expanded and/or transitioned from a first state to a second state that interfaces and/or couple with vessel(s) and/or tissue. The interfacing and/or coupling can allow the stent 508 to be secured within or around vessels or tissue. As the sheath, cover, or transport device 540 is removed from the stent 508, in at least one version, the stent 508 can expand or compress with the structural member(s) 530 and/or connection node(s) 532. The sheath, cover, or transport device 540 can be removed through an opening 527 in a vessel or tissue. The sheath, cover, or transport device 540 can include a needle 542 coupled to the sheath, cover, or transport device 540 directly or indirectly through wire, string or other connection mechanism, and/or perforation(s) 544.

Figure 6A:
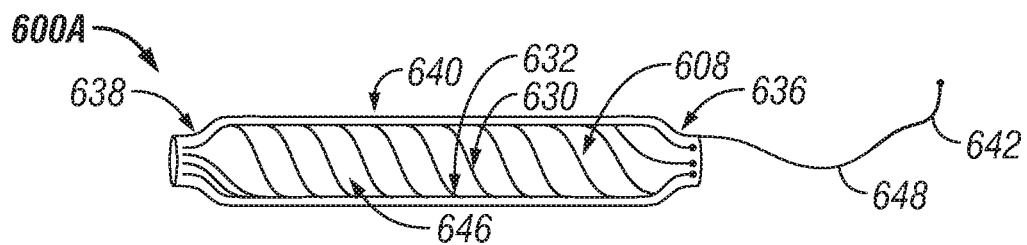
FIG. 6A is an illustration of an expandable stent with a wire cover.

FIG. 6A is an illustration of a stent delivery system 600A. The stent delivery system 600A can include a stent 608 and a sheath, cover, or transport device 640. The stent 608, in at least one example, includes end anchor(s) 638, connection node(s) 632, expandable members 630, counter expandable member(s) 646, and/or end anchor(s) 636. The connection node(s) 632, expandable member(s) 630, and/or counter expandable member(s) 646 can provide the structural support for the stent 608, defining a hollow tubular section and/or stent body. The end anchor(s) 636/638 can be coupled to the connection node(s) 632, expandable member(s) 630, and/or counter expandable member(s) 646 through fasteners, such as, but not limited to, screws, nails, bolts, adhesives, glues, or may be manufactured and/or formed with the connection node(s) 632, expandable member(s) 630, and/or counter expandable member(s) 646.

During an expansion the end anchor(s) 636/638 can expand, transition, and/or contract to allow for an interface with a vessel or tissue (not illustrated). The expandable member(s) 630, and/or counter expandable member(s) 646 can allow for an expansion, contraction, and/or compression to occur that can increase, or decrease the internal diameter of the stent 608. In at least one version, the sheath, cover, or transport device 640 compresses and/or contains a stent 608 that can expand. The sheath, cover, or transport device 640 can be removed via a needle 642 and/or an opening. The needle 642, in at least one version, would be coupled to the sheath, cover, or transport device 640 via a wire or thread 648.

Figure 6B:
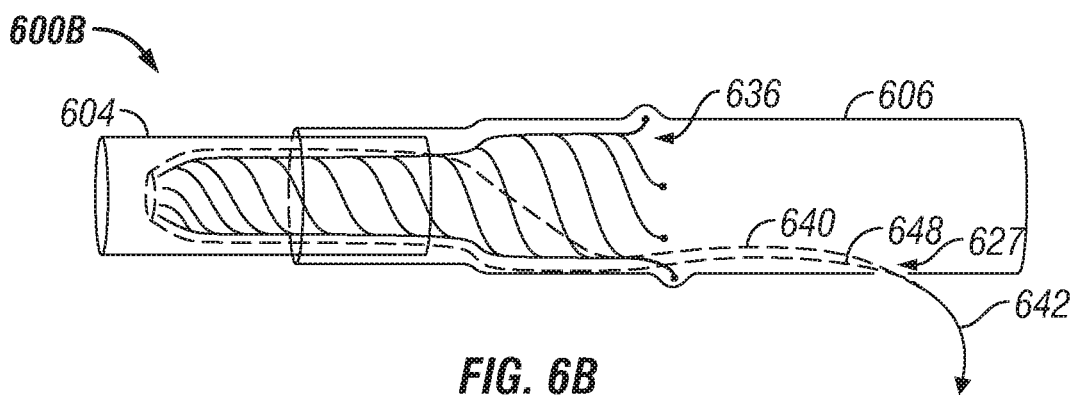
FIG. 6B is an illustration of an expandable stent in a partially expanded state.

FIG. 6B is an illustration of a stent delivery system 600B. The stent delivery system 600B can include a stent 608 and a sheath, cover, or transport device 640. The stent 608 can include, in at least one version, end anchor(s) 636/638. The end anchor(s) 636 and/or end anchor(s) 638 allow for an interfacing with a donor vessel 604 and/or a recipient vessel 606 that can secure the stent 608 within and/or around the vessels 604/606. In at least one version, the end anchor(s) 636/638 are contained, compressed, and/or expanded by a sheath, cover, or transport 640 that can prevent an expansion or compression of the stent 608 and/or end anchor(s) 636/638.

The sheath, cover, or transport device 640 can be removed from the stent 608 via an opening 627 in a vessel or tissue. In at least one version, the sheath, cover, or transport device 640 can be coupled to a needle 642 via a wire or thread 648 that allows the sheath, cover, or transport device 640 to be removed via an opening in a vessel or tissue.

Figure 7A:
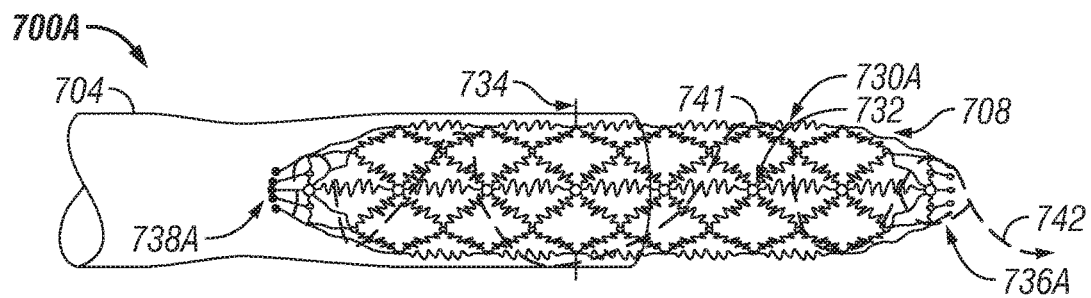
FIG. 7A is an illustration of an expandable stent with a wire cover.

FIG. 7A is an illustration of a stent delivery system 700A. The stent delivery system 700A can include a stent 708, and a sheath, cover, or transport device 741. In at least one version, the stent 708 can include end anchor(s) 736A, end anchor(s) 738A, body anchor(s) 734, connection node(s) 732, and/or structural member(s) 730A. The body anchor(s) 734 can allow the stent to be secured to a vessel or tissue, such as, but not limited to, a donor vessel 704 and/or a recipient vessel (not illustrated).

The sheath, cover, or transport device 741 can include a needle 742 to allow for the removal of the sheath, cover, or transport device 741 via an opening in a vessel or tissue. In at least one version, as the sheath, cover, or transport device 741 is removed it can allow for an expansion, contraction, or compression of the stent 708, and/or anchor(s) 734, 736A, 738A.

Figure 7B:
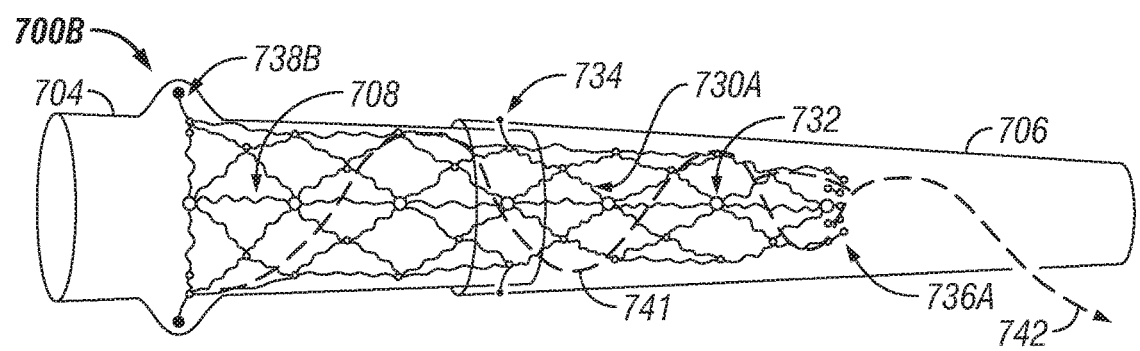
FIG. 7B is an illustration of an expandable stent in a first partially expanded state.

FIG. 7B is an illustration of a stent delivery system 700B. The stent delivery system 700B can allow a stent 708 to be delivered and/or transported to an operation or operation site and utilized during operations with relative ease. The stent delivery system 700B includes a sheath, cover, or transport device 741 that, in at least one example, can be removed from the stent 708 to allow for an expansion, contraction, or compression of the stent 708.

In at least one version, a donor vessel 704, and/or a recipient vessel 706 are coupled to the stent 708 via body anchor(s) 734. As the sheath, cover, or transport device 741 is removed from the stent 708 the end anchor(s) 738B can expand, contract, or transition to interface with a vessel or tissue, such as, but not limited to, a donor vessel 704. In addition, structural member(s) 730A can also begin to expand in those sections of the stent 708 that have had the sheath, cover, or transport device 741 removed. The connection node(s) 732 allow for the structural member(s) 730A to be coupled together and/or coupled to the anchor(s) 734, 736A, and/or 738B. Those sections of the stent 708 that are not expanded, and/or contracted the structural member(s) 730A remain in an unexpanded, uncontracted, and/or uncompressed state, until allowed to transition when the sheath, cover, or transport device 741 is removed.

In at least one version, the sheath, cover, or transport device 741 is a wire cover. The wire or thread cover can be strong enough to prevent the expansion, contraction, and/or compression of the stent 708, while also being flexible enough to be removed through vessel(s) or tissue. Some versions of the sheath, cover, or transport device 741 may also include sections to contain, expand, contract, and/or compress specific section of the stent 708, such as, but not limited to the anchor(s) 734, 736, and/or 738. The sheath, cover, or transport device 741 can be removed through an opening via a needle 742 or other removal device.

Figure 7C:
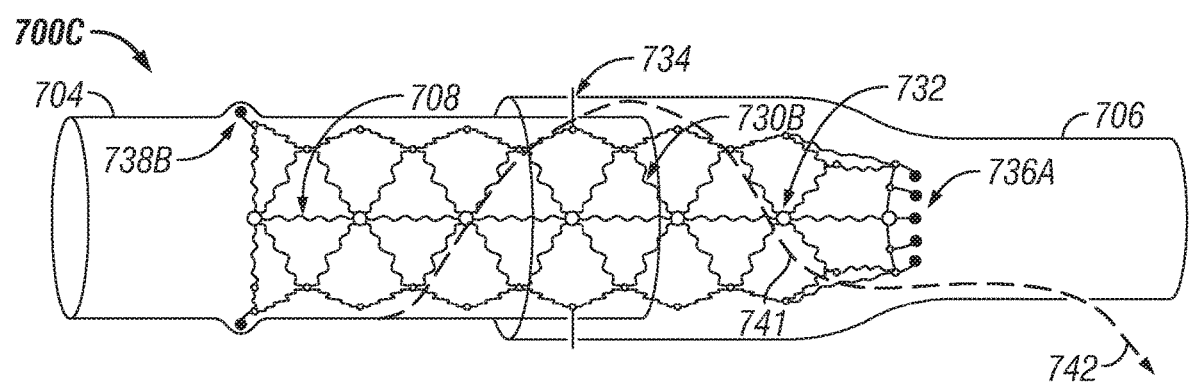
FIG. 7C is an illustration of an expandable stent in a second partially expanded state.

FIG. 7C is an illustration of a stent delivery system 700C. The stent deliver system 700C can include a stent 708 and a sheath, cover, or transport device 741. The stent 708 can include structural member(s) 730B that can be expandable, containable, and/or compressible, connection node(s) 732 that can couple the structural member(s) 730B and/or the anchor(s) 734, 736, and/or 738.

In at least one example, the structural member(s) 730B are allowed to expand after the removal of the sheath, cover, or transport device 741. As the structural member(s) 730B expand, contract, and/or compress the anchor(s) 734, 736, and/or 738 can expand, contract, and/or transition at a similar rate allow for an interface with vessel(s) and/or tissue securing the stent 708 in place. The vessel(s) and/or tissue can also be opened or restricted to assist in a healing and/or recovery process by the expansion, contraction, and/or compression. For example, the stent 708 can expand to allow for an increase in blood flow through vessel(s) and/or tissue. In other examples, the stent 708 can be utilized to contract or compress vessel(s) and/or tissue, to prevent further blood loss and/or fluid flow through the area of the vessel(s) and/or tissue.

The body anchor(s) 734, in at least one version, allow for a securing of the vessel(s) 704 and/or 706 to the stent 708. While illustrated coming radially outward from the outer surface of the stent 708, the body anchor(s) 734 can also in some versions can extend radially inward from the inner surface of the stent 708. The end anchor(s) 736, and/or 738 can also expand, contract, compress, and/or transition, directly or indirectly from the expansion, contraction, and/or compression of the structural member(s) 730B.

The expansion, contraction, and/or compression of the stent 708 can occur when the sheath, cover, or transport device 741 is removed from the stent 708. The sheath, cover, or transport device 741 may be coupled to a needle 742 to assist in the removal of the sheath, cover, or transport device 741 through an opening in the nearby vessel(s) and/or tissue.

Figure 7D:
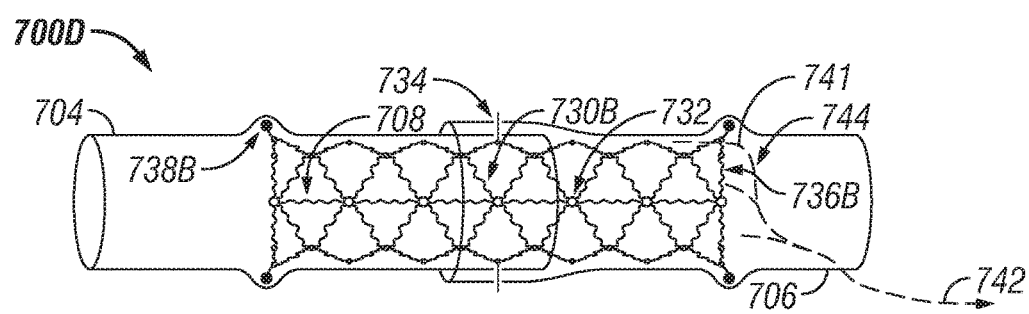
FIG. 7D is an illustration of an expandable stent in a fully expanded state.

FIG. 7D is an illustration of a stent delivery system 700D. The stent delivery system 700D can include a stent 708 and a sheath, cover, or transport device 741. In at least one version, the sheath, cover, or transport device 741 maintains the stent 708 in a compressed and/or contracted state prior to a deployment or use. In other versions, the sheath, cover, or transport device maintains the stent 708 in an expanded state prior to a deployment or use.

As the stent 708 expands, contracts, and/or compresses after the removal of the sheath, cover, or transport device 741, the anchor(s) 734, 736, and/or 738 may also expand, contract, and/or compress as well. In at least one version, the expansion, contraction, and/or transition of the anchor(s) 734, 736 and/or 738 can be proportional to the rate of expansion, contraction, and/or compression of the stent 708. In other versions, the expansion, contraction, and/or transition of the anchor(s) 734, 736 and/or 738 can be non-proportional to the rate of expansion, contraction, and/or compression of the stent 708.

In at least one example, when the stent 708 is fully expanded that anchor(s) 734, 736, and/or 738 interface and/or interact with the donor vessel 704 and the recipient vessel 706. The body anchor(s) 734 extend radially from the outer surface of the stent 708 to extend to and/or through the donor vessel 704, and/or recipient vessel 706. In at least one version, the body anchor(s) 734 are traumatic anchor(s) capable of piercing through one or more vessel(s) or tissue. In other versions, the body anchor(s) 734 are atraumatic anchor(s) capable of interacting and interfacing with vessel(s) and/or tissue in a manner that does not pierce through the vessel(s) and/or tissue.

Similarly, the end anchor(s) 736 and/or 738 can also respond in the same manner as the body anchor(s) 734. In at least one example, end anchor(s) 736 are atraumatic anchor(s) and end anchor(s) 738 are traumatic anchor(s). In other examples, the end anchor(s) 736 are traumatic anchor(s) and the end anchor(s) are atraumatic anchor(s), or both anchor(s) 736 and 738 are both atraumatic or traumatic anchor(s).

The sheath, cover, or transport device 741 can include sections 744 capable of coupling to the anchor(s) 734, 736, and/or 738 in addition to containing the stent 708. For example, at least one of the section(s) 744 may couple to the end anchor(s) 738 allowing them to be expanded, contracted, and/or transitioned as the sheath, cover, or transport 741 is removed. As the sheath, cover, or transport device 741 is removed the section(s) 744 may be coupled to the anchor(s) in a manner, such as, but not limited to, a string, suture, thread, wire, or other string and/or wire like materials include plastics, metals, carbon fiber, alloys, or combinations thereof. In at least one version, the section(s) 744 may pull the anchor(s) 736 and/or 738 in a manner that allows them to transition into an interfacing or interacting position against the vessel(s) and/or tissue. In some version, the section(s) 744 are removed with the sheath, cover, or transport device 741 via an opening, with a needle 742 or other removal device.

Figure 8A:
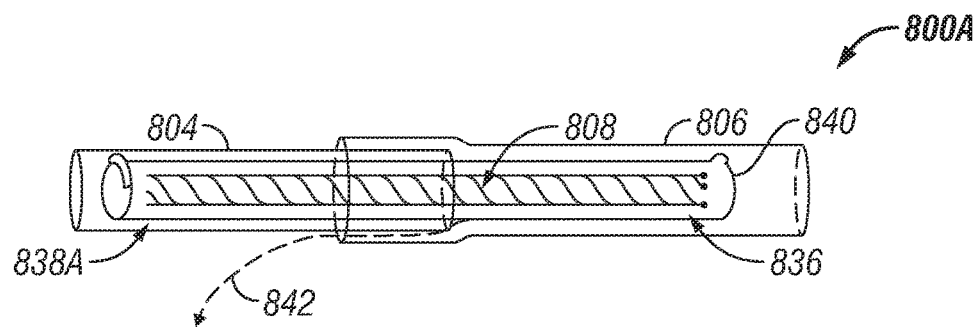
FIG. 8A is an illustration of an expandable stent within a donor and recipient vessel.

FIG. 8A is an illustration of an expandable stent 808 within a donor vessel 804 and recipient vessel 806. A stent delivery system 800A can include a stent 808 and a sheath, cover, or transport device 840. The sheath, cover, or transport device 840 can protect, and contain the stent 808 during transport and delivery during an operation. In at least one version, the stent 808 can be an expandable stent with an expansion, contraction, and/or compression from an accordion, twisting, and/or unwinding motion. The motion may be triggered by the removal of the sheath, cover, or transport device 840. The sheath, cover, or transport device 840 can be coupled to a needle 842 or other removal device. In at least one example, the sheath, cover, or transport device may be removed through the opening between the donor vessel 804 and the recipient vessel 806. Allowing the sheath, cover, or transport device 840 to be removed and limiting or avoiding any additional trauma to nearby vessel(s) and/or tissue.

The sheath, cover, or transport device 840 can also protect and/or contain the end anchor(s) 836 and/or 838. In at least one version, the sheath, cover, or transport device 840 can be coupled directly or indirectly to the end anchor(s) 836 and/or 838.

Figure 8B:
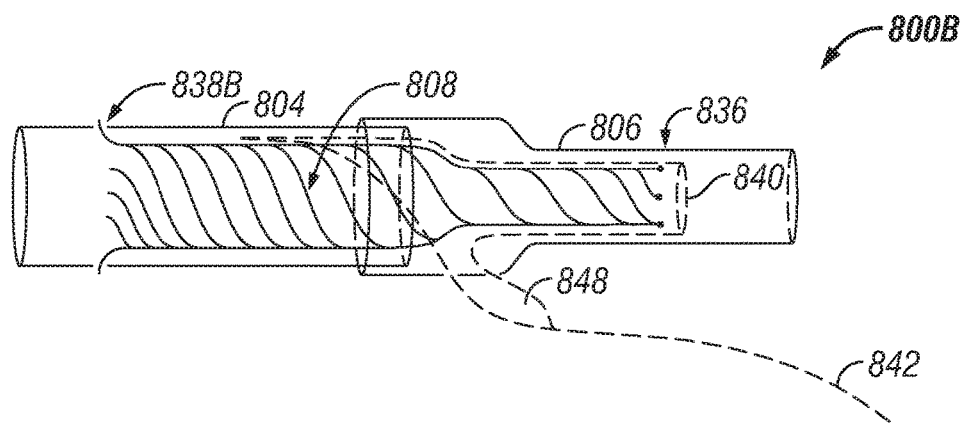
FIG. 8B is an illustration of an expandable stent is a partially expanded state.

FIG. 8B is an illustration of an expandable stent 808 is a partially expanded state. A stent delivery system 800B can include a stent 808 and a sheath, cover, or transport device 840. In at least one version, as the sheath, cover, or transport device 840 is removed, the stent 808 expands in an accordion, rotating, or twisting motion. As the stent 808 expands, the end anchor(s) 836 and/or 838 can also expand and/or transition to interface and/or interact with the donor vessel 804 and/or recipient vessel 806. The end anchor(s) 836 and/or 838 may in at least one version be a combination of atraumatic and traumatic anchor(s) or anchor point(s). In other versions, the end anchor(s) 836 and/or 838 may be traumatic or atraumatic anchor(s) respectively.

The sheath, cover, or transport device 840 can include fabric, plastic, carbon fiber, synthetic(s), alloys, metal, or combinations thereof. In at least one version, the sheath, cover, or transport device 840 can be a liner or wrap, that can also include section(s) or perforation(s) 848 that contains and/or prevent the stent from expanding and allow for the sheath, cover, or transport device to separate around the anchor(s) 836 and/or 838. The section(s) or perforation(s) 848 and/or the sheath, cover, or transport device 840 may also be coupled to a needle 842 or other removal device to assist in the removal of the sheath, cover, or transport device from nearby vessel(s) and/or tissue.

Figure 9A:
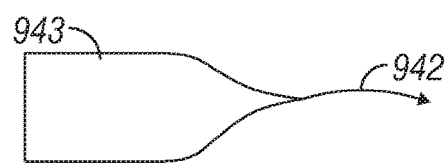
FIG. 9A is an illustration of a sheath or cover for a stent.

FIG. 9A is an illustration of a sheath, cover, or transport device 943 for a stent. The sheath, cover, or transport device 943 can have many different shapes, profiles, and/or attributes. In at least one example, the sheath, cover, or transport device 943 may be substantially rectangular and can be coupled to a needle 942 for ease of removal.

Figure 9B:
FIG. 9B is an illustration of a sheath or cover for a stent.

FIG. 9B is an illustration of a sheath, cover, or transport device 945 for a stent. The sheath, cover, or transport device 945 can have many different shapes, profiles, and/or attributes. In at least one example, the sheath, cover, or transport device 945 may be substantially oval and can be coupled to a needle 942 for ease of removal.

Figure 9C:
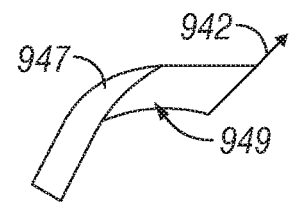
FIG. 9C is an illustration of a sheath or cover for a stent.

FIG. 9C is an illustration of a sheath, cover, or transport device 947 for a stent. The sheath, cover, or transport device 947, can have many different shapes, profiles, and/or attributes. In at least one example, the sheath, cover, or transport device 947 may be separated and/or perforated 949 to allow it to separate from the stent with ease. In at least one example, the sheath, cover, or transport device 945 may be substantially rectangular and/or comprised of one or more strips and can be coupled to a needle 942 for ease of removal.

Figure 10A:
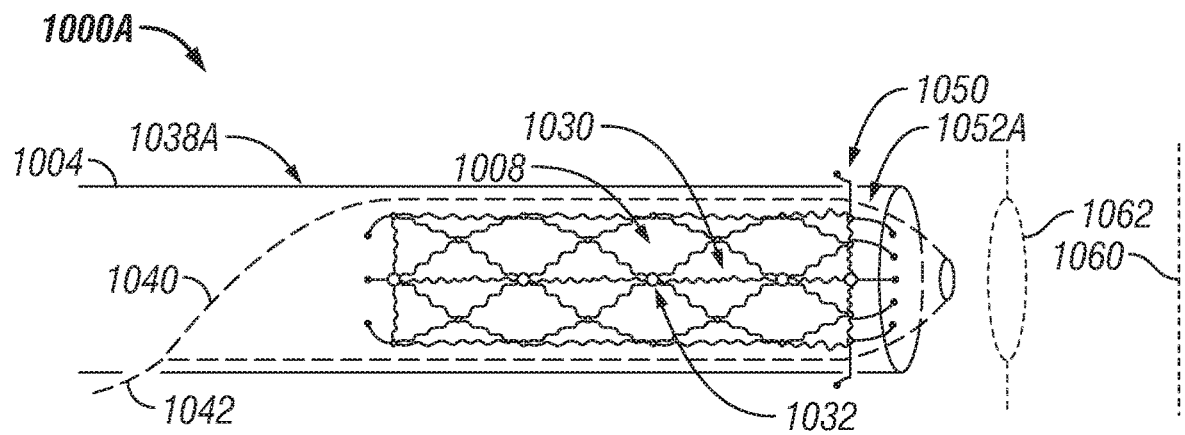
FIG. 10A is an illustration of an expandable stent with a sheath or cover.

FIG. 10A is an illustration of a stent delivery system 1000A with a stent 1008 in an unexpanded state. The stent delivery system may be utilized to allow a stent 1008 to be delivered through a donor vessel 1004. The stent 1008 can be surrounded and/or contained by a sheath, cover, or transport device 1040. The sheath, cover, or transport device 1040 can include many shapes, materials, and/or sizes. In at least one example, the sheath, cover, or transport device can be manufactured of plastic, biodegradable materials, cloth, fibers, synthetic fibers, carbon fiber, magnetic materials, metal, and/or other forms of manufacturing suited for use in surgical or other applications. In at least one example, the sheath, cover, or transport device 1040 may be coupled to a needle 1042. The needle 1042 may allow for ease of removal for the sheath, cover, or transport device 1040.

In at least one embodiment, the stent 1008 can be in an unexpanded state that allows for an unexpanded end anchor 1038A. The unexpanded end anchor 1038A can be traumatic and/or atraumatic. The unexpanded end anchor 1038A can be coupled to an expandable member 1030, and/or a connection node 1032. The expandable member 1030 and/or connection node 1032 can allow for the expansion and/or size and configuration of the stent 1008.

The stent 1008 can also have a locking anchor 1050 that extends radially from the stent 1008. In at least one example, the locking anchor(s) 1050 can be coupled to an expandable member 1030 and/or connection node 1032. An unexpanded securing anchor 1052A may be coupled to an expandable member 1030 and/or connection node 1032. The unexpanded securing anchor 1052A alone and/or in combination with the locking anchor 1050 can allow for the securing of the stent within a recipient vessel 1060. The stent 1008 may pass through an opening 1062 in a recipient vessel 1060 prior to and/or during the securing and/or locking.

Figure 10B:
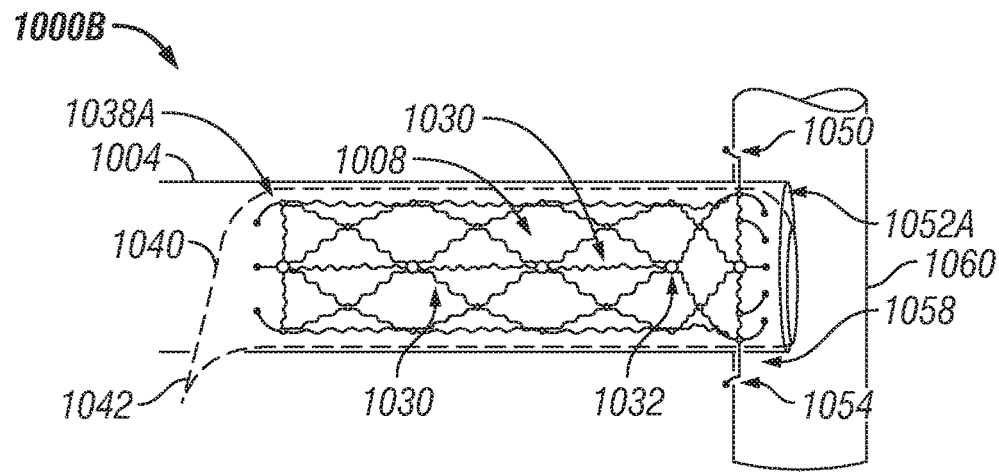
FIG. 10B is an illustration of an expandable stent within a recipient vessel.

FIG. 10B is an illustration of a stent delivery system 1000B with a stent 1008 in a locked state. A stent 1008 may by passed through a donor vessel 1004, to allow for a locking with a recipient vessel 1060. In at least one embodiment, during the locking state, and/or transition to a locking state a sheath, cover, or transport device 1040 for the stent 1008 may be removed and/or partially removed. In some examples, the sheath, cover, or transport device 1040 may be coupled and/or removed with a needles 1042.

In at least one embodiment, the stent 1008 can be in an unexpanded state that allows for an unexpanded end anchor 1038A. The unexpanded end anchor 1038A can be traumatic and/or atraumatic. The unexpanded end anchor 1038A can be coupled to an expandable member 1030, and/or a connection node 1032. The expandable member 1030 and/or connection node 1032 can allow for the expansion and/or size and configuration of the stent 1008.

The stent 1008 can also have a locking anchor 1050 that extends radially from the stent 1008. In at least one example, the locking anchor(s) 1050 can be coupled to an expandable member 1030 and/or connection node 1032. An unexpanded securing anchor 1052A may be coupled to an expandable member 1030 and/or connection node 1032. The unexpanded securing anchor 1052A alone and/or in combination with the locking anchor 1050 can allow for the securing of the stent within a recipient vessel 1060. The stent 1008 may pass through an opening 1062 in a recipient vessel 1060 prior to and/or during the securing and/or locking. The locking anchor 1050 can assist in securing the stent 1008 within the recipient vessel 1060. The securing may occur when the locking anchor(s) 1050 engage at locking engagement points 1054 along the recipient vessel 1060, a securing donor vessel section 1058 may also be passed through the opening with the locking anchor(s) 1050 and extend beyond the locking anchor(s) 1050 which pass through the wall of the donor vessel.

Figure 10C:
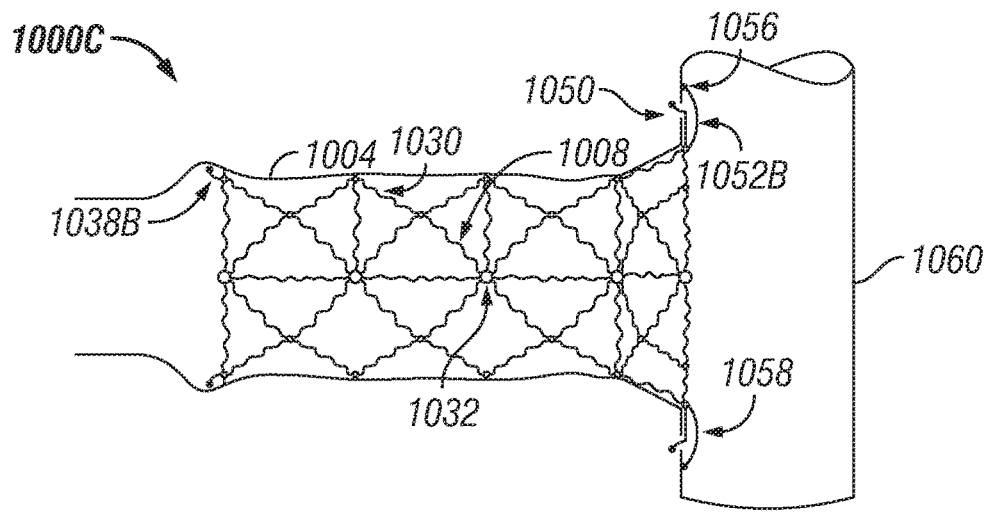
FIG. 10C is an illustration of an expandable stent in an expanded state.

FIG. 10C is an illustration of a stent delivery system 1000B with a stent 1008 in an expanded state and/or secured state. A stent 1008 may be passed through a donor vessel 1004 to be locked and/or secured with a recipient vessel 1060. In at least one embodiment, when the stent 1008 is locked and/or secured the stent 1008 can be expanded. The expansion can allow the expandable members 1030 and/or connection node(s) 1032 to interact with each other and/or other forces to be expanded. In some examples an expanded end anchor 1038B can assist in securing the stent 1008 to the donor vessel 1004.

The stent 1008 can also have a locking anchor 1050 that extends radially from the stent 1008. In at least one example, the locking anchor(s) 1050 can be coupled to an expandable member 1030 and/or connection node 1032. An expanded securing anchor 1052B can also be coupled to an expandable member 1030 and/or connection node 1032. The expanded securing anchor 1052B can utilized and/or expanded to assist in securing the donor vessel 1004 with the recipient vessel 1060. The securing donor vessel section 1058 can be secured over the locking anchor 1050 through a securing engagement point 1056. In at least one example, the securing donor vessel section 1058 allows for the closer of the recipient vessel openings and/or traumatic anchor and/or locking points.

Figure 11A:
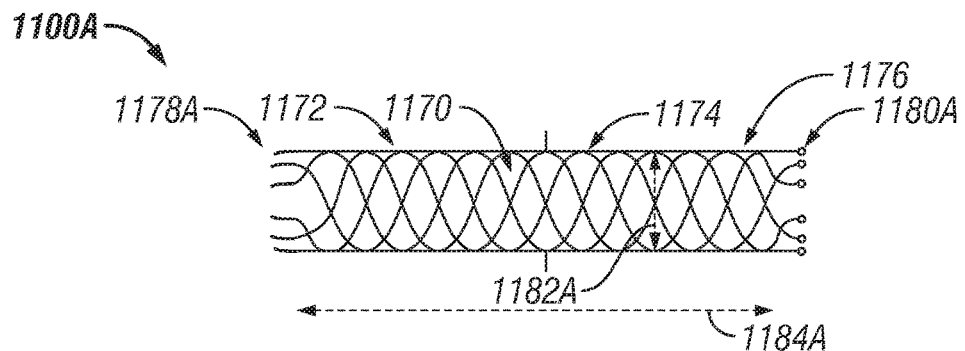
FIG. 11A is an illustration of an expandable stent in an unexpanded state.

FIG. 11A is an illustration of an expandable stent system 1100A in an unexpanded state. An expandable member and/or member(s) 1170 allow for the expansion and/or contraction and/or collapsing of the expandable stent system 1100A. In at least one embodiment, the expandable stent system 1100A may include a first expandable section 1172, a second expandable section 1174, and/or a third expandable section 1176. The expandable section may be expanded and/or manipulated independently or in combination.

A first unexpanded end anchor 1178A can be coupled to the first expandable section 1172, and a second unexpanded end anchor 1180A can be coupled to the second and/or third expandable section. In an expanded state, the unexpanded diameter 1182A may be smaller than during an expanded state. Correspondingly, an unexpanded length 1184 may also be smaller than the length in an expanded state.

Figure 11B:
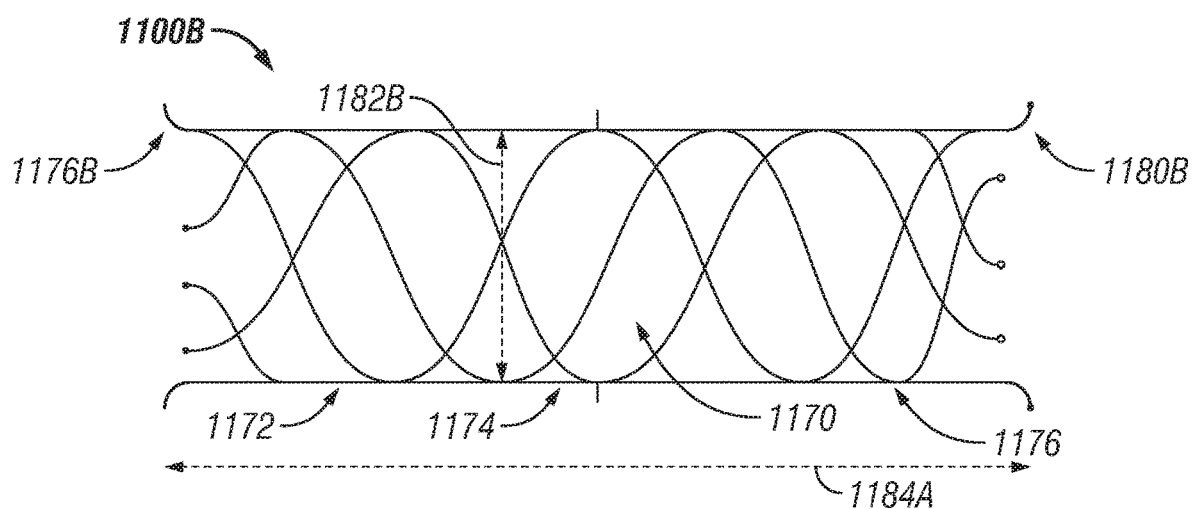
FIG. 11B is an illustration of an expandable stent in an expanded state.

FIG. 11B is an illustration of an expandable stent system 1100B in an expanded state. During expansion the expandable member 1170 may expand, and/or lengthen in one or both in length and/or diameter. In at least one embodiment, the expandable stent system 1100B may include a first expandable section 1172, a second expandable section 1174, and/or a third expandable section 1176. The expandable section may be expanded and/or manipulated independently or in combination.

The expansion may also cause an expanded end anchor 1178B and/or expanded end anchor 1180B to extend outwardly and/or away from the stent system 1100B in order to securing against a vessel (not illustrated). The expanded diameter 1182B and/or expanded length 1184B in at least one embodiment are greater than the diameter and/or length of the stent system in an unexpanded state.

While this invention has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While various embodiments in accordance with the principles disclosed herein have been described above, it should be understood that they have been presented by way of example only, and not limitation. Thus, the breadth and scope of this disclosure should not be limited by any of the above-described exemplary embodiments, but should be defined only in accordance with any claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, and by way of example, although the headings refer to a "Technical Field," the claims should not be limited by the language chosen under this heading to describe the so-called field. Further, a description of a technology as background information is not to be construed as an admission that certain technology is prior art to any embodiment(s) in this disclosure. Neither is the "Brief Summary of the Invention" to be considered as a characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure, but should not be constrained by the headings set forth herein.

I claim:

1. A stent delivery apparatus, comprising:
    a hollow tubular body with a proximal opening at a proximal end of the hollow tubular body and a distal opening at a distal end of the hollow tubular body, the proximal opening and the distal opening being defined by the hollow tubular body;
    a support rod capable of passing through the proximal opening and the distal opening; and
    a tip coupled to the support rod, and the tip is substantially oval shaped that can pass through the hollow tubular body;
    a sheath made of at least one material creating a barrier between a stent and the hollow tubular body of the stent delivery apparatus, and wherein the sheath is coupled to a needle.

2. The stent delivery apparatus of claim 1, wherein the hollow tubular body is configured to enclose and support the stent.

3. The stent delivery apparatus of claim 1, wherein the support rod comprises a first section and a second section.

4. The stent delivery apparatus of claim 3, wherein the first section is sized to support the stent, and the second section is sized to allow for a user to push the support rod.

5. The stent delivery apparatus of claim 1, wherein the tip has a first section and a second section.

6. The stent delivery apparatus of claim 5, wherein the first section is substantially cone shaped and affixed to the second section.

7. The stent delivery apparatus of claim 5, wherein the second section is substantially cylinder shaped and coupled to the support rod.

8. A stent delivery system, comprising:
    a hollow tubular body;
    a support rod capable of passing through the hollow tubular body;
    a stent that surrounds the support rod and is enclosed by the hollow tubular body; and
    a tip coupled to the support rod and capable of engaging with the stent, and wherein the tip can pass through the hollow tubular body;
    wherein the stent further comprises a hollow tubular stent body with at least one anchor expanding radially from the hollow tubular body;
    a sheath made of at least one material creating a barrier between the stent and the hollow tubular body of the stent delivery system, and wherein the sheath is coupled to a needle.

9. The stent delivery system of claim 8, wherein the hollow tubular body further comprises a proximal opening at a proximal end of the hollow tubular body.

10. The stent delivery system of claim 8, wherein the hollow tubular body further comprises a distal opening at a distal end of the hollow tubular body.

11. The stent delivery system of claim 8, wherein the support rod further comprises a first section and a second section.

12. The stent delivery system of claim 11, wherein the first section is sized to support the stent, and the second section is sized to allow for a user to push the support rod.

13. The stent delivery system of claim 11, wherein the first section is coupled to the tip.

14. The stent delivery system of claim 8, wherein the hollow tubular stent body defines a proximal opening at a proximal end of the stent, and defines a distal opening at a distal end of the stent.

15. The stent delivery system of claim 14, wherein the stent further comprises at least one anchor at the proximal end of the stent.

16. The stent delivery system of claim 14, wherein the stent further comprises at least one anchor at the distal end of the stent.

17. The stent delivery system of claim 1, wherein the sheath is configured to partially enclose the stent.

18. The stent delivery system of claim 1, wherein the sheath is configured to fully enclose the stent.

19. The stent delivery system of claim 1, wherein the sheath is coupled to a thread.

20. The stent delivery system of claim 1, wherein the sheath is coupled to a wire.

21. A stent delivery system, comprising:
a hollow tubular body for receiving and transporting a stent;
a support rod capable of passing through the hollow tubular body and supporting the stent during transport; and
a tip coupled to the support rod for engaging with the stent during delivery of the stent to a patient, wherein the tip is passed through the hollow tubular body;
wherein the stent has a hollow tubular stent body with at least one anchor extending radially from the hollow tubular body;
a sheath made of at least one material creating a barrier between the stent and the hollow tubular body of the stent delivery system, and wherein the sheath is coupled to a needle.

22. The stent delivery system of claim 21, wherein the hollow tubular body further comprises a proximal opening defined by the hollow tubular body at a proximal end of the hollow tubular body.

23. The stent delivery system of claim 21, wherein the hollow tubular body further comprises a distal opening defined by the hollow tubular body at a distal end of the hollow tubular body.

24. The stent delivery system of claim 21, wherein the stent is compressed to be received by the hollow tubular body through an opening defined by the hollow tubular body.

25. The stent delivery system of claim 21, wherein the stent has a hollow tubular stent body defining a plurality of openings.

26. The stent delivery system of claim 21, wherein the stent has a hollow tubular stent body defining a first opening at a first end of the stent.

27. The stent delivery system of claim 21, wherein the stent has a hollow tubular stent body defining a second opening at a second end of the stent.

28. The stent delivery system of claim 21, wherein the support rod further comprises a first section and a second section.

29. The stent delivery system of claim 28, wherein the first section is coupled to the tip, and the first section is coupled to the second section.

30. The stent delivery system of claim 28, wherein the first section is sized to support the stent, and the second section is sized to allow a user to move the support rod through the hollow tubular body.

31. The stent deliver system of claim 21, wherein the support rod is moved by a user in a first direction releasing the stent from the hollow tubular body.

* * * * *

UNITED STATES PATENT AND TRADEMARK OFFICE
CERTIFICATE OF CORRECTION

PATENT NO.        : 11,998,467 B2
APPLICATION NO.   : 16/752343
DATED             : June 4, 2024
INVENTOR(S)       : Spiros Manolidis Page 1 of 1

It is certified that error appears in the above-identified patent and that said Letters Patent is hereby corrected as shown below:

In the Claims

Column 15, Line 19, Claim 17, replace "system of claim 1" with --system of claim 9--.
Column 15, Line 21, Claim 18, replace "system of claim 1" with --system of claim 9--.
Column 15, Line 23, Claim 19, replace "system of claim 1" with --system of claim 9--.
Column 15, Line 25, Claim 20, replace "system of claim 1" with --system of claim 9--.

Signed and Sealed this
Seventh Day of January, 2025

Derrick Brent
*Acting Director of the United States Patent and Trademark Office*